United States Patent [19]
McDonald

[11] 3,943,770
[45] Mar. 16, 1976

[54] MIDSTREAM URINE SPECIMEN COLLECTION DEVICE

[76] Inventor: Bernard McDonald, 18212 Pacific Coast Highway, Malibu, Calif. 90265

[22] Filed: Nov. 6, 1974

[21] Appl. No.: 521,352

[52] U.S. Cl. ............................... 73/421 R; 4/110
[51] Int. Cl.² ............................................ G01N 1/10
[58] Field of Search ........ 73/421 R; 4/110; 128/2 F, 128/295

[56] References Cited
UNITED STATES PATENTS

| | | | |
|---|---|---|---|
| 3,635,091 | 1/1972 | Linzer | 73/421 R |
| 3,722,503 | 3/1973 | Hovick | 4/110 |
| 3,848,581 | 11/1974 | Cinqualbre | 128/2 F |

*Primary Examiner*—S. Clement Swisher
*Attorney, Agent, or Firm*—Christie, Parker & Hale

[57] ABSTRACT

A midstream urine sample collector in which three separate detachable containers are supported from and interconnected by a frame including a fluid passage which interconnects the three containers. The first container is a disposable bag of flexible material which connects to the fluid passage at a point lower than the connection of the passage to the other two containers. An inlet receiving a funnel directs the urine stream into the passage, the urine flowing into the first container because it is at the lowest level. Once the first container is filled, fluid flows through the passage into the second and third containers in that order. The second container is a removable centrifuge vial which can then be used to run the sample tests. Means is provided for cutting off flow of fluid in and out of the first container once it is filled to prevent contamination of the fluid in the second container, which receives the midstream sample.

10 Claims, 4 Drawing Figures

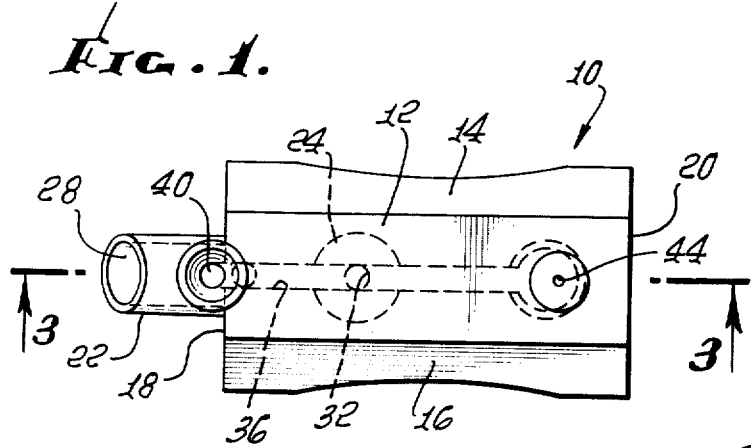
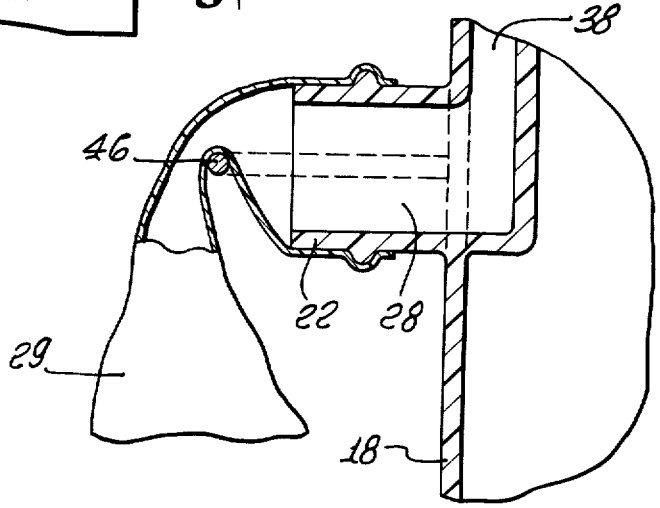
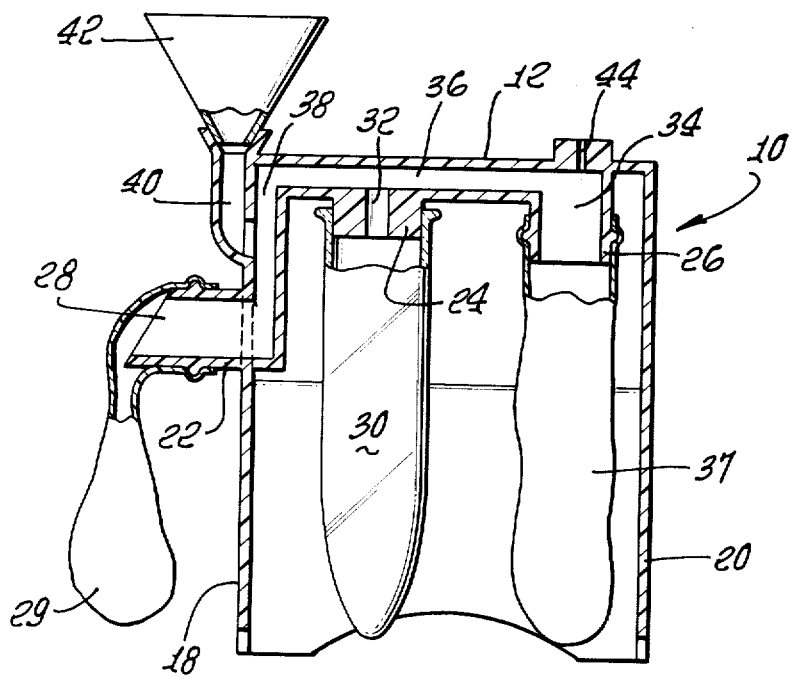
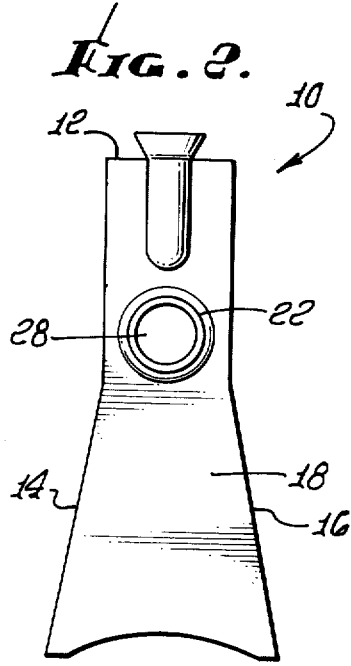

MIDSTREAM URINE SPECIMEN COLLECTION DEVICE

FIELD OF THE INVENTION

This invention relates to urine specimen collectors, and more particularly to a device for collecting a contamination-free midstream urine sample.

BACKGROUND OF THE INVENTION

In making tests on urine samples, it is necessary to collect a sample which is free of any contaminants. It is therefore desirable to collect the sample from midstream so that the urethra and other areas of the urinary tract can be flushed out by the initial stream. Because it is difficult or in some cases impossible for the patient to interrupt the stream so as to pass part of the stream before collecting the sample, it is desirable to have a urine collection device which automatically diverts a portion of the midstream into a specimen container for analysis without interruption of the stream by the patient. One such collection device is described in my copending application Ser. No. 363,383, filed May 24, 1973. However, there is a need for an inexpensive specimen collector which automatically collects a midstream sample and that is convenient to use and can be easily sterilized.

SUMMARY OF THE INVENTION

The present invention is directed to an improved midstream urine sample collection device which has no moving parts and which can be packaged in a minimal space. The present invention further provides a urine collection device in which the forestream and any excess after the midstream sample is taken is collected in disposable containers made of flexible material, while the midstream sample container is preferably a standard centrifuge vial or the like which can be easily sterilized and reused.

In brief, the collection device of the present invention includes a frame member having a fluid passage interconnecting three outlets. Three containers are detachably connected to the frame member at the three outlets. An inlet member provides a downwardly extending opening which connects into the fluid passage. The passage at the opening to the inlet member and the opening to the first container is positioned at a lower level than the fluid passage at the openings to the second and third containers. Thus fluid entering the inlet member first runs into the first container. Means is provided for interrupting the flow of fluid into the first container when a predetermined amount of fluid has been received in the inlet member to prevent any of the fluid in the first container from entering the second container and contaminating the sample.

DESCRIPTION OF THE DRAWINGS

For a better understanding of the invention reference should be made to the accompanying drawings, wherein:

FIG. 1 is a top view of the preferred embodiment of the present invention;

FIG. 2 is an end view;

FIG. 3 is a sectional view taken on the line 3—3 of FIG. 1; and

FIG. 4 is a partial view of an alternative embodiment of the invention.

DETAILED DESCRIPTION

Referring to the drawing in detail, the numeral 10 indicates generally the frame of the urine collection device which preferably is molded from a suitable plastic material capable of withstanding temperatures sufficient to produce sterilization. The frame includes a top wall 12, supporting side walls 14 and 16, and end walls 18 and 20. The side walls may be tapered outwardly at the bottom to provide a wide stable base for supporting the collection device on a flat horizontal surface.

On the underside of the top 12 there is molded a fluid conduit which interconnects three outlet nipples 22, 24 and 26. The outlet nipple 22 projects horizontally outwardly from the end wall 18 and is preferably cylindrical in shape to provide an outlet passage 28. The end of the outlet nipple 22 is terminated in a plane which extends at an angle to the axis of the nipple so that the bottom of the nipple projects out further from the side wall 18 then the top of the nipple. A disposable bag 29 of elastic material fits over the nipple and hangs downwardly from the nipple to receive any fluid from the passage 28.

The nipple 24 projects vertically downwardly from the inside of the top wall 12 and is adapted to receive a standard centrifuge tube 30, the open end of which is adapted to fit over the nipple 24. The tube may be either pressed in position on the nipple or be held by the standard half-turn bayonet lock type connection. The nipple 24 has a central passage 32 extending vertically and which is of substantially smaller diameter than the inside of the tube 30.

The third nipple 26 similarly projects downwardly from the inside of the top wall 12 and includes an opening or passage 34. The fluid conduit provides a passage 36 extending horizontally between the opening 34 and the nipple 26 and the opening 32 and the nipple 24. In addition, the fluid conduit provides a fluid passage 38 which extends between the opening 32 and the nipple 24 and the opening 28 and the nipple 22. A disposable bag 37 of elastic material fits over the nipple 26 to catch any fluid overflowing from the sample tube 30.

The urine sample is admitted to the fluid conduit by means of a vertically extending passage 40 which opens into the passage 38 at an intermediate level above the opening 28 but below the openings 32 and 34. A removable funnel 42, preferably made by rolling a flat sheet of pre-cut material into a conical shape and inserting the small end into the top of the passage 40, is provided.

In operation, the urine stream is directed into the funnel 42 which in turn directs it into the passage 40. The initial or forestream flows downwardly through the opening 28 in the nipple 22 into the first flexible container or bag 29 hanging on the end of the nipple 28. As the bag begins to fill with fluid, the weight of the fluid stretches the bag across the opening 28 so as to seal off the opening against further flow. The urine then rises in the passage 38 and flows through the opening 32 into the sample tube 30. When the tube 30 fills up, overflow goes into the flexible bag container 37 attached to the nipple 26. The bags 29 and 37 can then be removed and disposed of while the tube 30 is detached from the nipple 24 and dispatched to the laboratory for a urinalysis. It will be noted that the nipple 24 projects down into the tube 30 and, because of the relatively small opening 32, displaces a portion of the volume of the tube at the top. This insures that when the tube is removed, the level of fluid in the tube 30 drops sufficiently below the top of the tube to prevent or reduce the chance of spillage. An air vent 44 allows air to bleed off as the urine displaces the air in the containers.

An alternative arrangement for blocking flow of urine through the opening 28 into the first container is shown in FIG. 4. Here the container bag passes up over a beam 46 extending in front of the opening 28. The beam 46 is supported from the end wall 18 and acts to partially support the weight of the container. As the container fills with fluid, the weight of the fluid increases the force with which the flexible bag presses against the top of the beam 46. Thus the neck of the bag becomes pinched off after a predetermined amount of fluid enters the bag. Various other arrangements may be provided to achieve the same effect, such as providing a noose around the neck of the bag 29 which tightens as the weight of the fluid in the bag stretches the neck. Alternatively, a buoyant ball may be inserted in the bag, the ball rising in the bag as the level of fluid rises until the ball is wedged into the neck of the bag, cutting off further flow of fluid into the bag.

From the above description, it will be seen that a very simple device is provided for collecting midstream urine samples. The frame with its fluid passages can be molded of plastic material, for example, and made inexpensive enough that it could be a throwaway item. Alternatively, it may be made of a material which would be sufficiently durable in the presence of heat to permit sterilization and reuse. The first and third container bags are disposable, as is the funnel. The first bag is automatically sealed off when it is filled with a predetermined weight of fluid, preventing any of the forestream from flowing back up out of the container and contaminating the midstream sample collected in the tube 30.

What is claimed is:

1. Apparatus for collecting a urine sample comprising a frame member having a fluid passage, three containers detachably connected to the frame member, the passage opening into each of the three containers, an inlet member opening downwardly into the passage, the passage at the opening to the inlet member and the opening to the first container being lower than the passage at the openings to the second and third containers when the urine collecting apparatus is in normal operative position, whereby fluid entering the inlet member first runs into the first container, the opening to the second container being intermediate the opening to the first and third containers, whereby fluid entering the inlet member runs into the second opening to fill the second container before filling the third container, the first container being of flexible disposable material having a neck portion, the frame having a nipple forming the first opening with the open end of the neck of the first container fitting over the nipple, and means engaging the neck of the container to pinch off the neck under the weight of the fluid added to the first container.

2. Apparatus of claim 1 further including means interrupting flow of fluid to the first container when a predetermined amount of fluid has been received in the inlet member.

3. Apparatus of claim 1 wherein the third container is made of flexible disposable material.

4. Apparatus of claim 3 wherein the means engaging the neck comprises means forming an edge engaging the neck of the first container, the container hanging downwardly over the edge so that the weight of the container is partially supported by said last named means.

5. Apparatus of claim 1 wherein the second container is a sterile centrifuge sample vial.

6. Apparatus of claim 5 wherein the frame means includes means providing a fluid-tight connection to the sample vial, the connection means including means projecting into the vial from the frame means to displace part of the volume in the vial.

7. A midstream urine specimen collection device comprising a forestream container and a midstream container, rigid conduit means connected to the two containers, inlet means coupled to the conduit means for receiving the urine stream, the conduit means having a section between the inlet means and the midstream container that is higher than the level of the conduit means at any point between the inlet means and the forestream container when in the normal operating position, whereby fluid entering the inlet means flows first into the forestream container, the forestream container including a flexible neck connecting the container to the conduit means, and means forming a ridge across which the flexible neck passes between the container and the conduit means, the weight of fluid in the container pulling the neck against the ridge for pinching off the neck when the weight of fluid in the forestream container reaches a predetermined level.

8. The apparatus of claim 7 further including means responsive to the weight of fluid in the forestream container for interrupting flow in the forestream container when the forestream container has received a predetermined amount of fluid.

9. Apparatus of claim 8 further including overflow means connected to the conduit means for receiving fluid after the midstream container is filled.

10. A midstream urine specimen collection device comprising a forestream container, a midstream container, and an overflow container, rigid conduit means connected to the three containers at the top of the containers, the inlet conduit having a portion extending upwardly between the forestream and midstream containers, means coupled to the conduit means at an intermediate level along the upwardly extending portion for receiving the urine stream, and means responsive to the weight of fluid in the forestream container for sealing off flow between the conduit and the forestream container when the forestream container has received a predetermined weight of fluid.

* * * * *